United States Patent [19]
Casey

[11] Patent Number: 5,911,574
[45] Date of Patent: Jun. 15, 1999

[54] JAW FIXATION AND RELEASE SYSTEM FOR USE IN ORTHOGNATHIC SURGERY AND IN THE TREATMENT OF FRACTURED JAWS

[76] Inventor: Kevin M. Casey, 17722 Loop Rd., Holt, Mo. 64048

[21] Appl. No.: 08/919,555

[22] Filed: Aug. 28, 1997

[51] Int. Cl.⁶ .................................................. A61C 3/00
[52] U.S. Cl. .................. 433/19; 433/18; 433/24
[58] Field of Search ................... 433/18, 19, 22, 433/24, 10, 17

[56] References Cited

U.S. PATENT DOCUMENTS

| | | |
|---|---|---|
| 1,638,006 | 8/1927 | Aderer . |
| 1,797,481 | 3/1931 | Preston . |
| 2,481,177 | 9/1949 | Tofflemire . |
| 2,502,902 | 4/1950 | Tofflemire . |
| 3,262,207 | 7/1966 | Kesling ................................. 433/18 X |
| 3,505,736 | 4/1970 | Brader et al. ........................ 433/22 X |
| 3,775,850 | 12/1973 | Northcutt ............................. 433/22 X |
| 3,874,080 | 4/1975 | Wallshein ............................ 433/17 X |
| 4,202,328 | 5/1980 | Sukkarie . |
| 4,230,104 | 10/1980 | Richter . |
| 4,311,463 | 1/1982 | Glattly . |
| 4,478,577 | 10/1984 | Warren, Jr. ........................... 433/18 X |
| 4,872,449 | 10/1989 | Beeuwkes, III . |
| 5,035,614 | 7/1991 | Greenfield ........................... 433/18 X |
| 5,087,202 | 2/1992 | Krenkel . |
| 5,647,743 | 7/1997 | Schmitt ................................. 433/22 X |

OTHER PUBLICATIONS

Othodontic Supply & Equipment Division Sales Catalog, pp. 1, 4–6 (date unknown).

Primary Examiner—Nicholas D. Lucchesi
Attorney, Agent, or Firm—Shook, Hardy & Bacon L.L.P.

[57] ABSTRACT

A quick-release system is provided for fixing the upper and lower jaws of a patient together. The system includes at least one elongated release bar that is supported by a plurality of first brackets secured to the teeth of one of the jaws. Each first bracket is sized for receipt on a single tooth and includes a base, a pair of opposing tie wings protruding from an outer surface of the base, and a rigid loop of bracket material connected to the base and defining an opening extending in a direction transverse to the longitudinal axis of the base. The opening is sized for receipt of the release bar so that the release bar is supported loosely by the loops and can be removed from the loops by gripping an end of the release bar and pulling on it. An adhesive is used to secure the inner surfaces of the first brackets to separate teeth on one of the jaws of the patient with the openings in the loops of the first brackets generally aligned with one another so that the release bar is supported by the loops of the first brackets when the release bar is inserted through the aligned loops. A first arch wire is connected to the teeth on the jaw opposite the jaw on which the first brackets are secured, and a plurality of tie wires are tied between the release bar and the arch wire to hold the jaws shut. By pulling the release bar from the loops, the tie wires are released, and the jaws are free to move apart from one another.

7 Claims, 3 Drawing Sheets

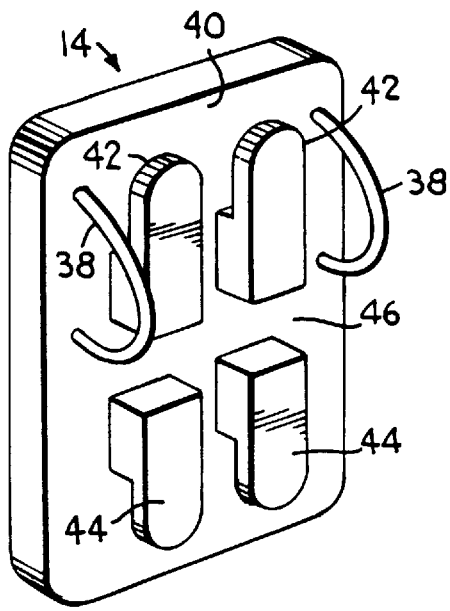
Fig.5.
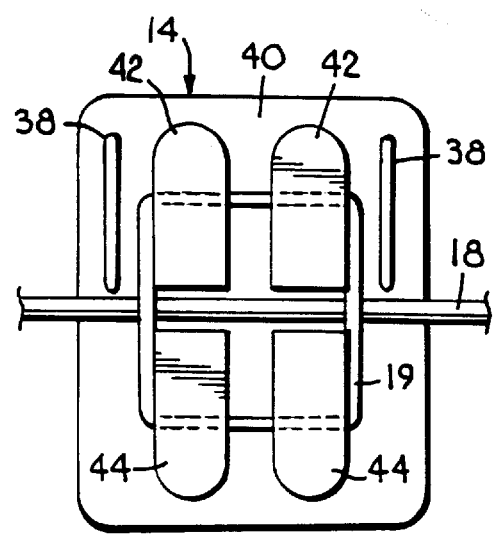
Fig.6.
Fig.7.
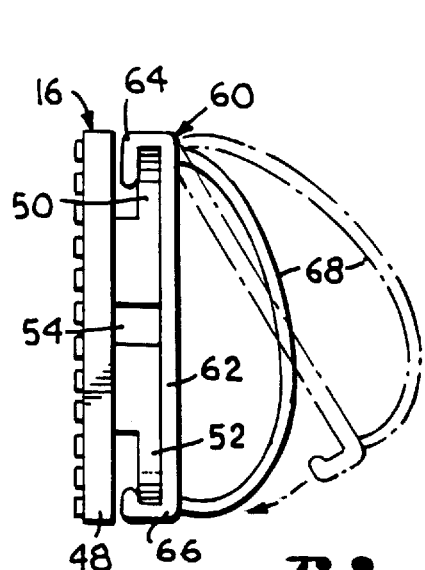
Fig.8.
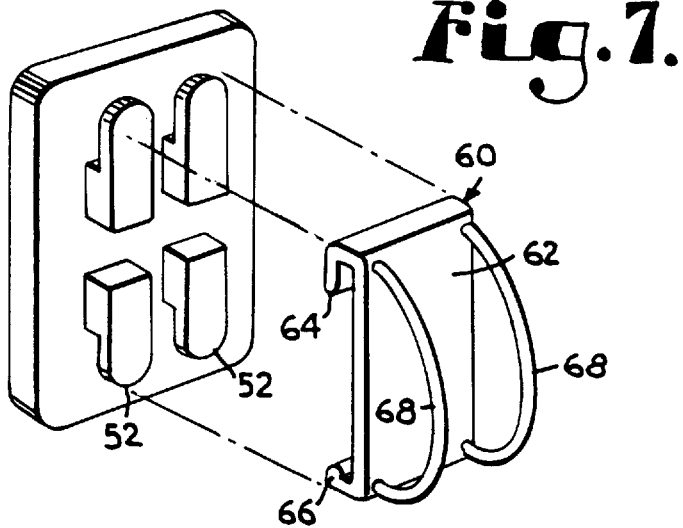

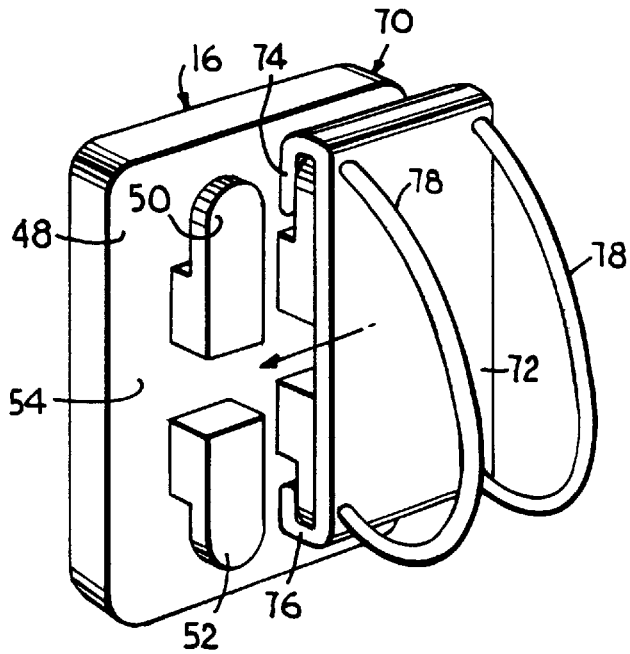
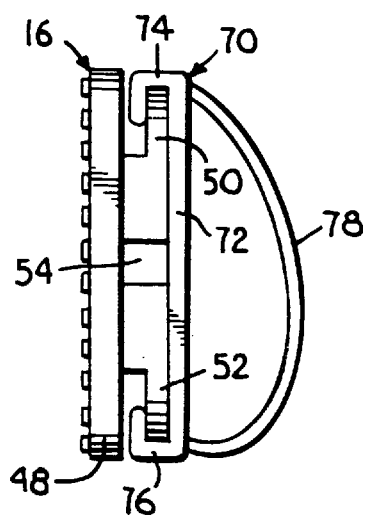
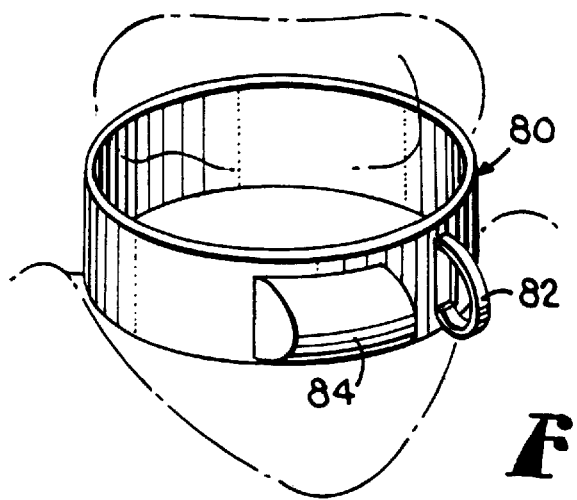

JAW FIXATION AND RELEASE SYSTEM FOR USE IN ORTHOGNATHIC SURGERY AND IN THE TREATMENT OF FRACTURED JAWS

BACKGROUND OF THE INVENTION

1. Field of the Invention

The present invention relates generally to the art of oral and maxillofacial surgery, and more particularly to a system for fixing the opposed jaws of a higher animal together subsequent to surgery while enabling quick release of the jaws after a period of healing or in the event of an emergency.

2. Discussion of the Prior Art

In the treatment of dentofacial deformities such as mandibular or maxillary excess or deficiency, it is known to employ presurgical periodontics, restorative dentistry and orthodontics, along with surgery, to remove the deformity. Typically, presurgical periodontic and restorative dentistry steps are completed first, followed by the placement of braces by an orthodontist who adjusts the positioning of the teeth so that they will be properly oriented upon completion of the surgery. Once these preliminary steps are completed, surgery is performed on the patient to remove the deformity, e.g. by removing excess bone and/or shifting portions of the mandible or maxilla relative to one another, and the jaws of the patient are wired together to immobilize them during healing. Subsequently, the jaws are released for movement, and post operative orthodontics are continued until such time as the teeth are properly aligned.

It is conventional to wire the jaws together by securing ball hooks to the arch wires and then tying bands or wires between the ball hooks of the opposing rows of teeth. However, such ball hooks must be individually placed on and secured to the arch bars, and may interfere with any post-surgical adjustments that must be made to the arch wires by an orthodontist. In addition, removal of the bands and ball hooks subsequent to healing of the mandibular and/or maxillary regions, or in the event of an emergency, requires independent removal of each band or wires. As such, several steps are required to release the jaws for movement apart from one another, and any quicker release is not possible.

An alternate means for providing ball hooks on opposing rows of teeth includes the provision of special brackets that are manufactured with protruding ball hooks to which bands can be tied. Although such brackets eliminate the problem of post operative adjustment of the arch wires, quick release of the jaws remains a problem.

SUMMARY OF THE INVENTION

It is an object of the present invention to provide a system for fixing the opposed-jaws of a higher animal together subsequent to surgery in such a way that the jaws can be quickly and easily released for movement apart from one another after a period of healing or in the event of an emergency. It is another object of the invention to provide a novel bracket capable of use in such a jaw fixation system, and to provide an attachment that can be used in conjunction with a conventional bracket to adapt the conventional bracket for use in such a system.

Another object of the invention is to provide a method of fixing the opposed jaws of a higher animal together in such a way that they can be easily released for movement apart from one another upon the removal of a single pair of release bars.

In accordance with these and other objects evident from the following description of a preferred embodiment of the invention, a jaw fixation system includes at least one elongated release bar having a proximal end provided with a gripping portion, and a plurality of first brackets secured to the teeth of one of the jaws by an adhesive. Each first bracket is sized for receipt on a single tooth and includes a base defining a longitudinal axis and presenting opposed inner and outer surfaces, a pair of opposing tie wings protruding from the outer surface of the base and extending over the base in a direction parallel to the longitudinal axis, and a rigid loop of bracket material connected to the base and defining an opening extending in a direction transverse to the longitudinal axis.

The opening in the loop is sized for receipt of the distal end of the release bar so that when the brackets are adhered to separate teeth on one of the jaws of the patient, the openings in the loops are generally aligned with one another so that the release bar can be inserted through and supported by the loops. A first arch wire is connected to the teeth on the jaw opposite the jaw on which the first brackets are secured, and a plurality of tie wires are tied between the release bar and the arch wire to fix the jaws against movement apart from one another. In order to release the jaws, the release bar is pulled from the loops.

By providing a system in accordance with the present invention, numerous advantages are realized. For example, by employing a bracket construction having one or more loops for guiding receipt of a release bar, it is possible to tie the release bar to the opposing jaw to fix the jaws together. Yet, it is easily possible to release the jaws for movement away from one another simply by pulling the release bar from the brackets, freeing the tie wires from the jaw on which the release bar was supported.

Preferably, the bracket includes one or more loops, each defining an opening of a diameter substantially greater than the diameter of the release bar so that the release bar is loosely supported by the loops during use of the system. As such, it is possible for the release bar to be pulled through the loops without binding. Alternately, an attachment can be provided for adapting a conventional bracket for use in a quick release system, wherein the attachment includes a body defining a longitudinal axis and presenting opposed inner and outer surfaces, upper and lower gripping elements for removably securing the body on the bracket, and at least one rigid loop connected to the body and defining an opening extending in a direction transverse to the longitudinal axis of the body. By employing an attachment constructed in accordance with the present invention, it is possible to remove the attachments upon removal of the release bar, leaving only conventional orthodontic braces in place during subsequent treatment.

BRIEF DESCRIPTION OF THE DRAWING FIGURES

The preferred embodiment of the present invention is described below with reference to the attached drawing figures, wherein:

FIG. 5 is a perspective view of an alternate construction of the first bracket;

FIG. 6 is a front elevational view of the alternate first bracket construction shown in FIG. 5;

FIG. 7 is an exploded perspective view of a conventional orthodontic bracket and an attachment constructed in accordance with the preferred embodiment;

FIG. 8 is a side elevational view of the bracket and attachment shown in FIG. 7, illustrating placement of the attachment on the bracket during use;

FIG. 9 is a perspective view of a conventional orthodontic bracket and an alternate attachment construction made in accordance with the preferred embodiment;

FIG. 10 is a side elevational view of the bracket and attachment shown in FIG. 9; and FIG. 11 is a perspective view of a band constructed in accordance with the preferred embodiment.

DETAILED DESCRIPTION OF THE PROFFERED EMBODIMENT

Figure 1:
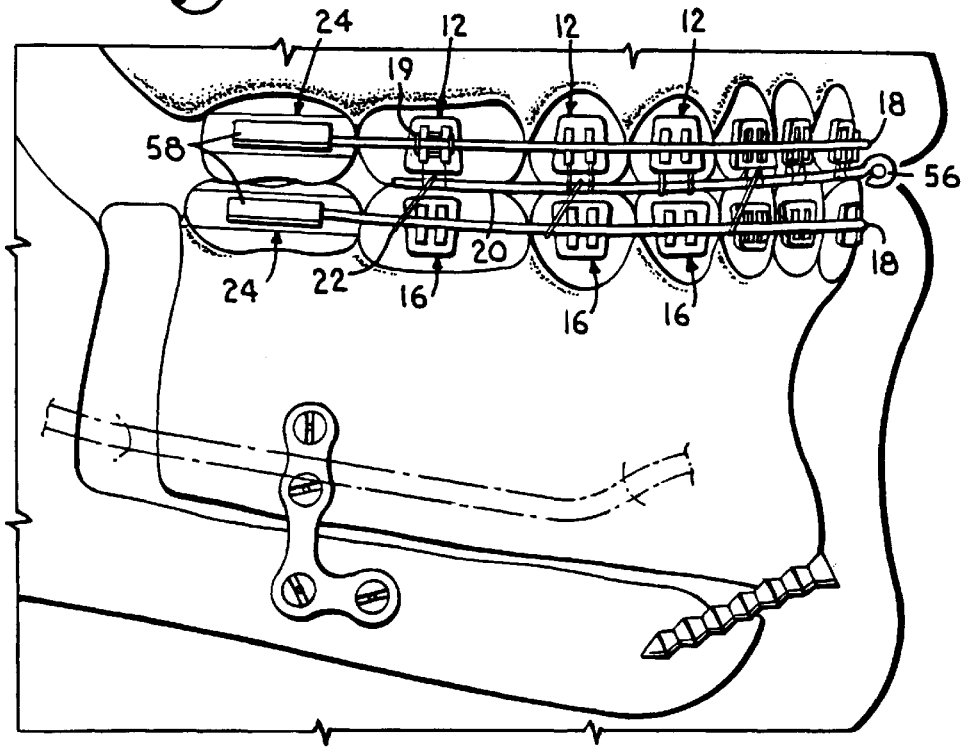
FIG. 1 is a schematic view of a human mandible and maxilla/midface area, illustrating a quick-release fixation system constructed in accordance with the preferred embodiment.

A human mandible and maxilla/midface area is shown in FIG. 1, immediately subsequent to mandible advancement surgery, wherein a quick-release fixation system is in place on the upper and lower rows of the patient's teeth for substantially immobilizing the mandible and maxilla relative to one another to prevent them from pulling apart during healing. Although the preferred system is described in connection with this one type of procedure, it is also useful in other types of dentofacial surgery, as well as in the treatment of fractured jaws and other procedures in which similar immobilization of the jaws is desired.

Figure 2:
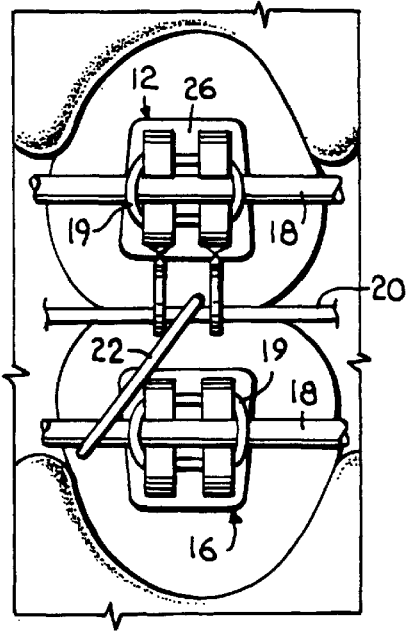
FIG. 2 is a fragmentary view of the system, illustrating a pair of opposed first and second brackets forming a part thereof.

The preferred system broadly includes a set of first brackets 12 adhered to all or some of the maxillary teeth, a set of second brackets 16 adhered to all or some of the mandibular teeth, upper and lower arch wires 18 received on the sets of first and second brackets and retained thereon by a plurality of elastic bands 19, shown in FIG. 2, a pair of release bars 20 supported by the set of first brackets, and a plurality of tie wires 22 extending between each release bar and the lower arch wire for fixing the mandible shut against movement away from the maxilla. In addition, as shown in FIG. 1, a pair of bands 24 are secured to the maxillary and mandibular second molars, and receive the posterior ends of the upper and lower arch wires.

Figure 3:
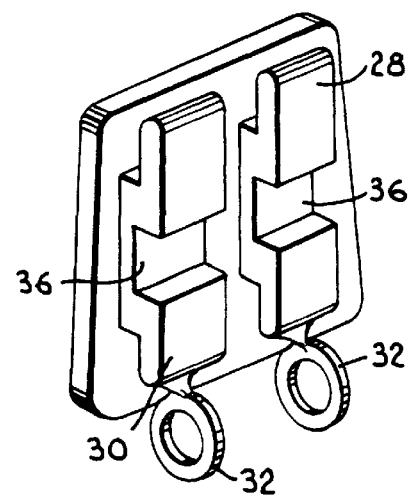
FIG. 3 is a perspective view of a first bracket constructed in accordance with the preferred embodiment.
Figure 4:
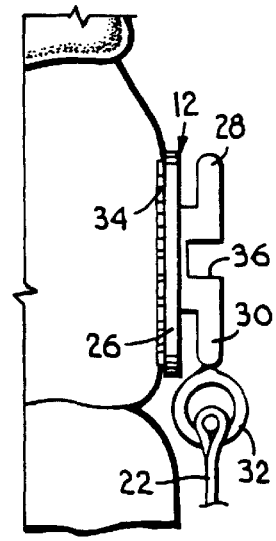
FIG. 4 is a side elevational view of the first bracket shown in FIG. 3, illustrating placement of the bracket during use.

As shown in FIG. 3, each first bracket 12 is sized for receipt on a single tooth, and includes a base 26 defining a vertical longitudinal axis adapted to extend in a direction parallel to the longitudinal axis of the tooth on which the bracket is secured, two laterally spaced pairs of longitudinally extending upper and lower tie wings 28, 30, and a pair of loops 32. The base 26 is preferably curved about an axis transverse to the longitudinal axis to conform to the convex shape of the tooth on which it is to be adhered, presenting a concave inner surface that is textured or grooved to facilitate use of the bracket with a conventional adhesive 34 for adhering the bracket to a tooth, as shown in FIG. 4. The base includes an outer surface opposite the inner surface, and the tie wings and loops are mounted on the outer surface, protruding away from the tooth on which the bracket is adhered.

Each pair of tie wings 28,30 presents two arms that extend longitudinally of the body in opposite directions to one another, and each arm is spaced from the outer surface of the base by a distance sized for receipt of one of the elastic bands. In addition, as shown in FIG. 3, each pair of tie wings is spaced laterally of the other to define a small space therebetween. A generally horizontally extending channel 36 is formed intermediate the tie wings of each tie wing pair and is dimensioned to receive the upper arch wire 18 so that the arch wire can be supported in the channel and secured to the bracket by one of the elastic bands. As shown in FIG. 2, in order to secure the arch wire in place, one of the elastic bands 19 is stretched over the arch wire 18 and hooked to the tie wings 28, 30.

As illustrated in FIG. 3, each of the loops 32 is formed as a rigid extension of one of the tie wings, and is preferably formed of the same material as the bracket, e.g. a suitable metal, synthetic resin or ceramic material. Each loop presents an opening extending in a horizontal direction transverse to the longitudinal axis of the base, and each opening is of a diameter substantially greater than the diameter of the release bars 20 so that one of the release bars is loosely received in and supported by the loop. In addition, the loops are thin so that the length of each opening is very short. As such, the loops present a minimal surface area to the release bars to prevent binding of the release bars upon removal thereof.

An alternate first bracket construction is illustrated in FIG. 5, wherein loops 38 project directly from the outer surface of the base 40 beyond the tie wings 42, 44, each of the loops including an elongated piece of curved bracket material presenting upper and lower ends that are welded or otherwise affixed to the base to define a rigid loop construction capable of supporting the release bars 20 during use. As shown in FIG. 6, in this alternate construction of the first bracket 14, the loops 38 are displaced longitudinally from the transverse channel 46 so as to avoid interfering with placement of the upper arch wire during presurgical orthodontic procedures carried out on the patient. The loops 38 could also be attached to the base 40 or tie wings 42, 44 of the bracket at any other location that permits the bracket to be utilized both as an orthodontic brace and as a support for the release bar used to fix the mandible against movement away from the maxilla.

Returning to FIG. 1, the set of second brackets 16 adhered to the mandibular teeth are conventional orthodontic brackets adapted to support the lower arch wire 18. As shown in FIG. 7, each of the second brackets 16 are sized for receipt on a single tooth, and include a base 48 defining a vertical longitudinal axis, and two laterally spaced pairs of longitudinally extending tie wings 50, 52. The base 48 is preferably curved about an axis transverse to the longitudinal axis to conform to the convex shape of the tooth on which it is to be adhered, presenting a concave inner surface that is textured or grooved to facilitate use of the bracket with a conventional adhesive for adhering the bracket to a tooth. The base 48 includes an outer surface opposite the inner surface, and the tie wings 50, 52 are mounted on the outer surface, protruding away from the tooth on which the bracket is adhered.

Each pair of tie wings 50,52 presents two arms that extend longitudinally of the body in opposite directions to one another, and each arm is spaced from the outer surface of the base by a distance sized for receipt of one of the elastic bands. In addition, a generally horizontally extending channel 54 is formed intermediate the tie wing pairs and is dimensioned to receive the lower arch wire so that the arch wire can be supported in the channel and secured to the bracket by one of the elastic bands. In order to secure the arch wire in place, one of the elastic bands is stretched over the arch wire and hooked to the arms of the tie wings.

Returning to FIG. 1, the release bars 20 are preferably formed of the same material as the arch wires 18, although it is preferred to form each bar from a piece of wire having a slightly larger diameter than the arch wires. In addition, each release bar includes a proximal end that is provided with a gripping element 56 such as a looped piece of wire or an elastic end cap received on the proximal end of the bar to permit manipulation thereof. As with the arch wires 18, the release bars 20 are flexible enough to conform to the curvature of the jaw as they are inserted into the loops of the brackets, as described below.

Each of the bands 24 is conventional, presenting a longitudinal opening sized for receipt over one of the molars of the patient, and including a tube or loop 58 within which the end of one of the arch wires 18 is received. The tubes 58 of the bands 24 enclose the distal ends of the arch wires, preventing the wires from poking the cheeks or gums of the patient.

In use, the system serves several purposes, including providing braces that can be used in presurgical and post-surgical orthodontic procedures to properly position the teeth relative to any reorientation or placement of the mandible or maxilla, as well providing a mechanism for permitting the mandible to be fixed or immobilized relative to the maxilla. The initial step carried out in use of the system includes adhering the sets of first and second brackets 12, 16 to the maxillary and mandibular teeth using a conventional adhesive. Once the brackets are properly set, the upper and lower arch wires 18 are fitted in the channels of the brackets and secured in place by the elastic bands applied over the arch wires to the tie wings of each bracket. With the brackets and arch wires so assembled, any desired presurgical orthodontic steps can be completed to re-orient the teeth in preparation for the changes to be made in surgery, and the surgery is performed.

Immediately upon completion of the surgery, the mandible is wired to the maxilla by inserting the release bars 20 through the loops of the first brackets 12 along each side of the patient's mouth and tying tie wires 22 between the release bars and the lower arch wire 18, synching the jaws shut to prevent the mandible from pulling away from the maxilla. Such fixation of the jaws immobilizes them against relative movement, facilitating the healing process. At any time during this fixation, it is possible to perform post-surgical orthodontic work on the patient by manipulating the arch wires in a conventional fashion, and the release bars 20 and tie wires 22 do not interfere with such manipulation.

Once the healing period is over, or in the event of an emergency requiring separation of the jaws, the tie wires 22 are released from the release bars 20 by gripping the elements 56 at the proximal ends of the release bars and pulling the bars from the loops of the first brackets 12. Thus, in one simple step, the mandible is released for movement independent of the maxilla, leaving the tie wires tied to the lower arch wire so that they do not fall freely into the mouth or throat of the patient. In addition, the brackets and arch wires remain in place on the teeth so that any follow-up orthodontic work can easily be performed.

As an alternative to employing the set of first brackets that are formed integrally with loops, it is possible to employ a conventional bracket similar to the second brackets 14, as shown in FIG. 7, in combination with a novel attachment 60 that adapts the conventional bracket for use in the preferred system. An example of an attachment suitable for such use is illustrated in FIG. 7, and broadly includes a body 62 defining a longitudinal axis and presenting opposed inner and outer surfaces, and upper and lower gripping elements 64, 66 for removably securing the body on the bracket. In addition, the body supports a pair of laterally spaced rigid loops 68 that define coaxial openings extending in a direction transverse to the longitudinal axis of the body.

The body 62 is preferably formed of the same material as the bracket, although any suitable metal, synthetic resin or ceramic material can be used, and is shaped to conform generally to the shape of the outer surface of the tie wings of the bracket so that the body is supported by the tie wings when fitted on the bracket. The gripping elements 64, 66 can take any suitable form, but are illustrated as including upper and lower L-shaped flanges, each of which defines a channel sized for receipt of the tie wings 50, 52 when the body is positioned on the bracket 16.

In the embodiment of FIG. 7, the channel defined by the upper flange 64 is deeper than that of the lower flange, and the distance between the upper and lower flanges is less than the combined length of the tie wings 50, 52. As shown in FIG. 8, the body 62 is fitted on the bracket by first inserting the upper flange 64 into the space between the upper tie wing 50 and the outer surface of the bracket base 48, and then flexing the body and snapping the lower flange 66 over the lower tie wing 52 into place between the lower tie wings and the base of the bracket.

Alternately, as shown in FIG. 10, flanges 72, 74 can be provided on an attachment 70 which are of the same dimensions as one another, defining channels that are spaced from one another by a distance substantially equal to the combined length of the upper and lower tie wings 50, 52. As such, the body 72 of the attachment 70 is fitted on the bracket 16 by sliding the attachment onto the tie wings from the side.

Regardless of the type of gripping elements employed, the attachment 60, 70 includes the loops 68, 78 which are constructed the same and perform the same function as the loops of the brackets described above. In order to use the attachments 60, 70 in a mandible fixation system, they are fitted on either the upper or lower row of brackets after the brackets are adhered to the teeth and the arch wires are secured in place and adjusted. Thereafter, the release bars 20 are inserted into the aligned loops of the attachments along each side of the patient's mouth, and tie wires are tied between the release bars and the opposing arch wire to prevent the mandible from pulling away from the maxilla.

In order to release the mandible for movement, the release bars 20 are simply pulled from the loops and the tie wires are cut from the lower arch wire. In addition, the attachments are removed from the brackets so that the only structure remaining in the patient's mouth is conventional orthodontic hardware.

A band 80 constructed in accordance with the preferred embodiment of the invention is illustrated in FIG. 11, and includes a pair of laterally spaced loops 82, 84 that are oversized relative to the release bars so as to accommodate the release bars during use of the jaw fixation system. The band 80 is designed for use on the posterior molars of the patient, and functions to receive the distal end of one of the release bars to support the release bar during jaw fixation. If desired, the posterior loop 84 of the band can be constructed as a tube that receives and encloses the distal end of the release bar. As such, the tube protects the end of the release bar and prevents injury to the surrounding gums and tissue. Preferably, the tube is closed at the posterior end thereof to prevent the distal end of the release bar from protruding beyond the tube.

Although the invention has been described with reference to the preferred embodiment illustrated in the attached drawing figures, it is noted that substitutions may be made and equivalents employed herein without departing from the scope of the invention as recited in the claims. For example, bands 80, as shown in FIG. 11, could be used in place of the first brackets and serve as the first brackets in the preferred method. In such an embodiment, both loops of each band would be open to permit receipt of the release bar through the loops.

What is claimed is:

1. A quick-release system for fixing the upper and lower jaws of a patient together, wherein each jaw supports a row of teeth, the system comprising:

an elongated release bar having a proximal end provided with a gripping portion, and a distal end;

a plurality of first brackets adapted to be secured to the teeth of one of the jaws, each first bracket being sized for receipt on a single tooth and including a base defining a longitudinal axis and presenting opposed inner and outer surfaces, a pair of opposing tie wings protruding from the outer surface of the base and extending over the base in a direction parallel to the longitudinal axis, and a rigid loop of bracket material connected to the base and defining an opening extending in a direction transverse to the longitudinal axis, the opening being sized for receipt of the distal end of the release bar;

an adhesive for securing the inner surfaces of the first brackets to separate teeth on one of the jaws of the patient with the openings in the loops of the first brackets generally aligned with one another so that the release bar is supported by the loops of the first brackets when the release bar is inserted through the aligned loops;

a first arch wire connected to the teeth on the jaw opposite the jaw on which the first brackets are secured; and a plurality of tie wires tied between the release bar and the arch wire, the release bar being removable from the loops and tie wires by pulling on an end of the release bar such that the jaws are free to move apart from one another.

2. A quick release system as recited in claim 1, wherein each first bracket includes structure defining a channel intermediate the tie wings that extends in a direction transverse to the longitudinal axis and parallel to the opening in the loop, the system further comprising a second arch wire supported in the channels of the first brackets.

3. A quick release system as recited in claim 2, wherein the length of the opening of each first bracket is smaller than the length of the channel.

4. A quick release system as recited in claim 1, wherein each first bracket includes a pair of rigid loops of bracket material that are spaced from one another and present openings that are coaxial, each opening being sized for receipt of the distal end of the release bar.

5. A quick release system as recited in claim 1, further comprising a plurality of second brackets secured to the teeth on the jaw opposite the jaw on which the first brackets are secured, each second bracket being sized for receipt on a single tooth and including a base defining a longitudinal axis and presenting opposed inner and outer surfaces, a pair of opposing tie wings protruding from the outer surface of the base and extending over the base in a direction parallel to the longitudinal axis, and a channel intermediate the tie wings that extends in a direction transverse to the longitudinal axis, the first arch wire being supported in the channels of the second brackets.

6. A quick release system as recited in claim 1, wherein each first bracket includes an attachment on which the loop is provided, the attachment including a body defining a longitudinal axis and presenting opposed inner and outer surfaces, and upper and lower gripping elements for gripping the tie wings to connect the body to the first bracket, the rigid loop being fixed to the body and defining an opening extending in a direction transverse to the longitudinal axis of the body, the opening being sized for receipt of the distal end of the release bar.

7. A method of releasably fixing the opposing jaws of a patient together, wherein each jaw supports a row of teeth, the method comprising the steps of:

securing first brackets to a plurality of the teeth on one of the jaws and second brackets to a plurality of the teeth on the opposing jaw, the first brackets each including a base defining a longitudinal axis and presenting opposed inner and outer surfaces, and a rigid loop supported by the base and defining an opening extending in a direction transverse to the longitudinal axis, the openings each being of a predetermined diameter;

securing an arch wire to the second brackets; inserting a release bar into the loops of the first brackets, the release bar being of a diameter substantially smaller than the diameter of each opening so that the release bar is loosely supported by the loops, and including a proximal gripping portion by which the release bar can be manipulated;

tying the arch wire and the release bar together so that the jaws are prevented from pulling apart from one another while the release bar is positioned in the loops, the release bar being removable from the loops by pulling the gripping portion of the bar so that the tie wires are released and the jaws are free to move apart from one another.

\* \* \* \* \*